(12) United States Patent
Patterson

(10) Patent No.: US 6,461,356 B1
(45) Date of Patent: *Oct. 8, 2002

(54) MEDICAL DEVICE HAVING AN INCREMENTALLY DISPLACEABLE ELECTRODE

(75) Inventor: Donald Patterson, North Chelmsford, MA (US)

(73) Assignee: C.R. Bard, Inc., Murray Hill, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/346,094

(22) Filed: Jul. 1, 1999

(51) Int. Cl.$^7$ .............................................. A61B 18/18
(52) U.S. Cl. ........................................... 606/41; 606/1
(58) Field of Search ................................ 606/1, 41, 42, 606/45–50; 607/101, 102, 115, 116

(56) References Cited

U.S. PATENT DOCUMENTS

| | | | | |
|---|---|---|---|---|
| 5,281,197 A | * | 1/1994 | Arias et al. | 604/57 |
| 5,458,597 A | * | 10/1995 | Edwards et al. | 606/41 |
| 5,643,319 A | * | 7/1997 | Green et al. | 606/218 |
| 5,853,409 A | * | 12/1998 | Swanson et al. | 606/31 |
| 5,928,252 A | * | 7/1999 | Steadman et al. | 606/148 |
| 6,178,354 B1 | | 1/2001 | Gibson | 607/116 |
| 6,280,441 B1 | * | 8/2001 | Ryan | 606/45 |

* cited by examiner

Primary Examiner—Michael Peffley
(74) Attorney, Agent, or Firm—Darby & Darby

(57) ABSTRACT

A medical device in one embodiment includes an electrode which is connected to a flexible, tubular, movable member, such as a catheter shaft or an outer sheath, which is slidably extended over a guide wire, flexible shaft, or other tubular member. A displacement mechanism is connected to the movable member, and may be actuated one or more times to displace the movable member in successive, predetermined increments, for creating a linear lesion or for performing diagnostic functions.

12 Claims, 3 Drawing Sheets

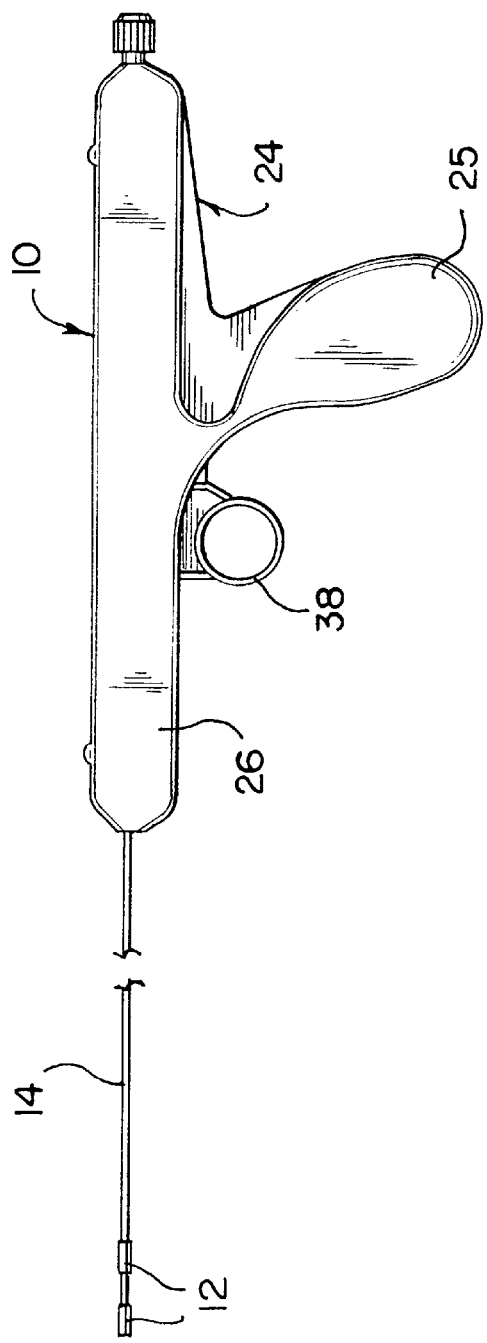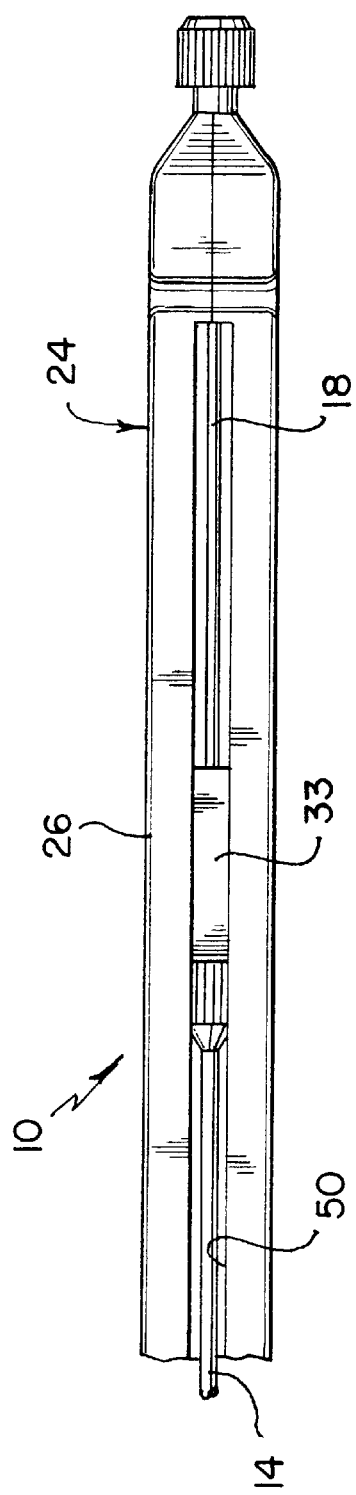

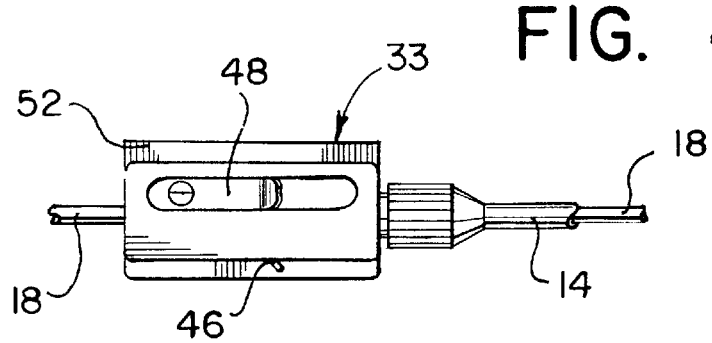
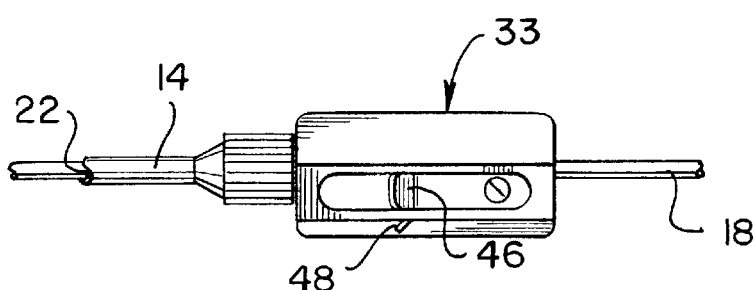
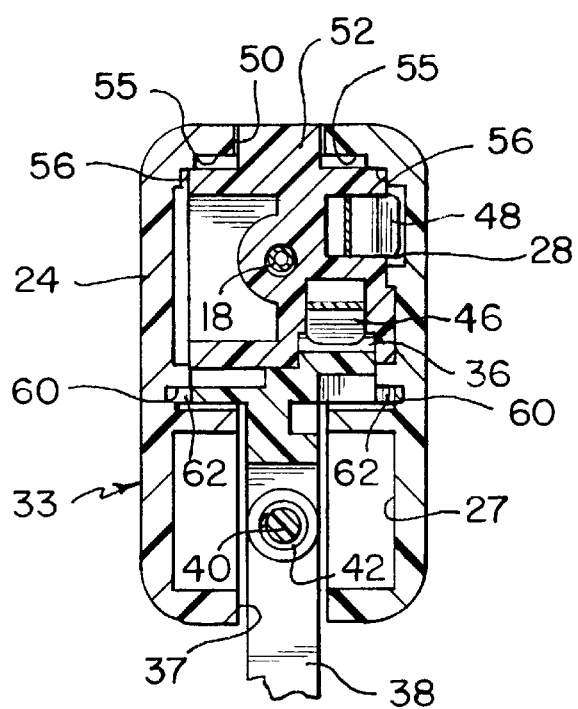
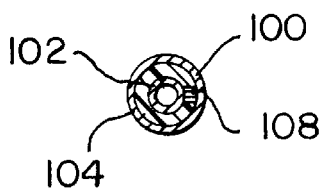
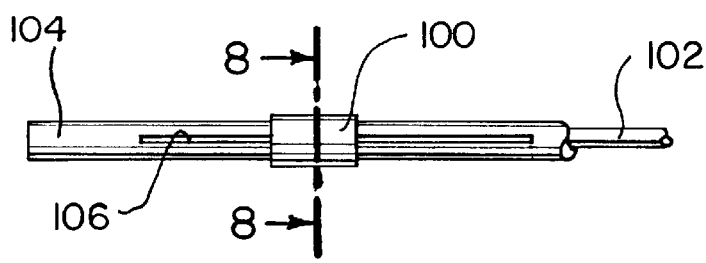

MEDICAL DEVICE HAVING AN INCREMENTALLY DISPLACEABLE ELECTRODE

FIELD OF THE INVENTION

This invention relates to medical devices for performing diagnostic, mapping, ablation, and other procedures and, more particularly, to a medical device for incrementally moving an electrode a predetermined distance.

BACKGROUND OF THE INVENTION

Cardiac arrhythmias (commonly known as irregular heart beats or racing hearts) are the result of various physical defects in the heart itself. One such defect comprises an extraneous strand of muscle fiber in the heart that provides an abnormal short-circuit pathway for electric impulses normally existing in the heart. This accessory pathway often causes the electric impulses that normally travel from the upper to the lower chamber of the heart to be fed back to the upper chamber, causing the heart to beat irregularly and therefore inefficiently pump blood.

Another common type of cardiac arrhythmia is ventricular tachycardia (VT), which may be a complication resulting from a heart attack or from a temporary reduction of blood supply to an area of heart muscle. VT is often caused by a tiny lesion, typically on the order of one to two millimeters, that is located close to the inner surface of the heart chamber. That lesion is often referred to as an "active site", because it does not fire in sequence with the rest of the heart muscle. VT causes the heart's normal rhythmic contraction to be altered, thereby affecting heart function. A typical symptom is rapid, inefficient heart beats.

Other common cardiac arrhythmias include atrial flutter and atrial fibrillation, which originate in the atria and cause the atria to beat so rapidly that they quiver (i.e., fibrillate). This in turn causes the ventricles to beat too fast (up to 200 beats per minute), which results in an inefficient pumping of blood.

Non-surgical procedures, such as management with drugs, have been proposed for treating cardiac arrhythmias. However, some arrhythmias are not treatable with drugs. For example, drug therapy to combat VT is typically successful in only 30 to 50 percent of patients. Because of this low success rate, another conventional remedy is to perform a surgical procedure in which various incisions are made in the heart to block conduction pathways, and thereby divide the atrial area available for multiple wavelet reentry in an effort to abolish the arrhythmia. Alternatively, an automatic implantable cardioverter/defibrillator (AICD) can be surgically implanted into the patient, as described in U.S. Pat. No. 4,817,608 to Shapland et al. While these surgical procedures can be curative, they are associated with increased morbidity and mortality rates, and are extremely expensive. Even the use of an AICD requires major surgical intervention. Moreover, patients of advanced age or illness often cannot tolerate invasive surgery to excise the tachycardia focus which causes the arrhythmia. Thus, this type of treatment is unavailable to many.

Non-surgical, minimally invasive techniques have been developed which are used to locate cardiac regions responsible for the cardiac arrhythmia, and to disable the short-circuit function of these areas. According to these techniques, electrical energy shocks are applied to a portion of the heart tissue to ablate that tissue and produce scars which interrupt the reentrant conduction pathways. The regions to be ablated are usually first determined by endocardial mapping techniques. Mapping typically involves percutaneously introducing a diagnostic catheter, having one or more electrodes, into the patient, passing the diagnostic catheter through a blood vessel (e.g., the femoral vein or aorta) and into an endocardial site (e.g., the atrium or ventricle of the heart), and inducing a tachycardia so that a continuous, simultaneous recording can be made with a multichannel recorder at each of several different endocardial positions. When a tachycardia focus is located, as indicated in the electrocardiogram recording, it is marked by means of a fluoroscopic image so that the site can be ablated. A conventional electrode catheter, having electrodes with a greater surface area than the diagnostic catheter's electrodes, can then provide electrical energy to the tissue adjacent the electrode to create a lesion in the tissue. One or more suitably positioned lesions will create a region of necrotic tissue to disable the malfunction caused by the tachycardia focus.

Conventional catheter ablation techniques have used catheters each having a single electrode fitted at its tip as one electrical pole. The other electrical pole is conventionally provided by a backplate in contact with a patient's external body part to form a capacitive coupling of the ablation energy source (DC, laser, RF, etc.). Other ablation catheters are known in which multiple electrodes are provided.

Ablation is carried out by applying energy to the catheter electrodes once the electrodes are in contact with the cardiac tissue. The energy can be, for example, RF, DC, ultrasound, microwave, or laser radiation. When RF energy is delivered between the distal tip of a standard electrode catheter and a backplate, there is a localized RF heating effect. This creates a well-defined, discrete lesion slightly larger than the tip electrode (i.e., the "damage range" for the electrode), and also causes the temperature of the tissue in contact with the electrode to rise.

To overcome certain types of cardiac arrhythmia, such as atrial flutter and atrial fibrillation, it is often necessary to create a long, continuous lesion (i.e., a linear lesion) to block the aberrant pathway(s). One conventional ablation procedure for creating linear lesions is commonly referred to as a "drag" method. According to that method, an ablation catheter carrying one or more ablation electrodes is manipulated through a patient's blood vessels to a desired location within the patient's heart. One or more of the electrodes is manipulated into contact with the heart tissue. Ablation energy is then delivered to the electrode(s), causing them to heat up and scar the adjacent tissue to create a lesion which is typically slightly larger than the surface area of the electrode contacting the tissue (the electrode's damage range). After the electrode has been disposed in that location for a sufficient time to ablate the adjacent tissue, the clinician then manually moves the catheter a selected amount by pulling on the catheter shaft, and ablation energy is again delivered to the electrode(s) to ablate the tissue that is then adjacent to the electrode. By continuing this procedure, the clinician attempts to create a continuous, linear lesion to block an aberrant pathway.

However, to create a continuous lesion, the clinician must be careful not to move the catheter too far between successive ablations. If the clinician should accidentally move the catheter too far, then the lesion created will not be continuous, and the aberrant pathway may not be destroyed, requiring that the patient undergo yet another procedure, which is inefficient and undesirable.

Accordingly, it will be apparent that there continues to be a need for a device for performing ablations which ensures the creation of linear lesions, by automatically displacing an ablation electrode in successive, incremental movements of a predetermined distance. In addition, the need exists for a device which moves an electrode in known increments to perform other medical procedures. The instant invention addresses these needs.

SUMMARY OF THE INVENTION

According to one aspect of the invention, an electrode is connected to a movable member, such as a catheter shaft or an outer sheath, which is slidably extended over a guide wire, flexible shaft, or other tubular member. A displacement mechanism is connected to the movable member, and may be actuated one or more times to displace the movable member in successive, predetermined increments. In this manner, the electrode is reliably moved in constant increments, and is suitable for creating a linear lesion or for performing diagnostic functions, without forcing the clinician to estimate the distance the electrode has been moved.

Thus, in one illustrative embodiment, the present invention is directed to a medical device comprising an elongated shaft, an electrode mounted on the shaft, and an electrode displacement mechanism connected to the shaft and operative to displace the shaft in predetermined increments.

In another illustrative embodiment, the invention is directed to a method for creating continuous lesions, comprising: (a) positioning an ablation electrode at a selected site within a patient, the ablation electrode having predetermined dimensions; (b) delivering ablation energy to the electrode to ablate the patient's tissue disposed adjacent to the tissue; (c) displacing the electrode in a predetermined increment, wherein the predetermined increment is determined based upon one or more of the dimensions of the electrode; and (d) repeating steps (b) and (c) one or more times to create a continuous lesion.

DESCRIPTION OF THE DRAWINGS

Other objects, features and advantages of the invention discussed in the above summary of the invention will be more clearly understood from the following detailed description of preferred embodiments, which are illustrative only, when taken together with the accompanying drawings in which:

FIG. 1 is a side elevation view of a mechanism for incrementally displacing an electrode according to one illustrative embodiment of the present invention;

FIG. 2 is a fragmented top plan view of the mechanism shown in FIG. 1;

FIG. 4 is a fragmented side view of a ratchet mechanism included in the mechanism shown in FIG. 1;

FIG. 5 is a bottom view of the ratchet mechanism shown in FIG. 4;

FIG. 6 is a cross-sectional view taken along the line 6—6 of FIG. 3 and looking in the direction of the arrows;

FIG. 7 is a fragmented side view of another illustrative embodiment of the mechanism for incrementally displacing an electrode according to the present invention; and FIG. 8 is a cross-sectional view taken along the line 8—8 of FIG. 7 and looking in the direction of the arrows.

DETAILED DESCRIPTION OF THE PREFERRED EMBODIMENTS

Figure 3:
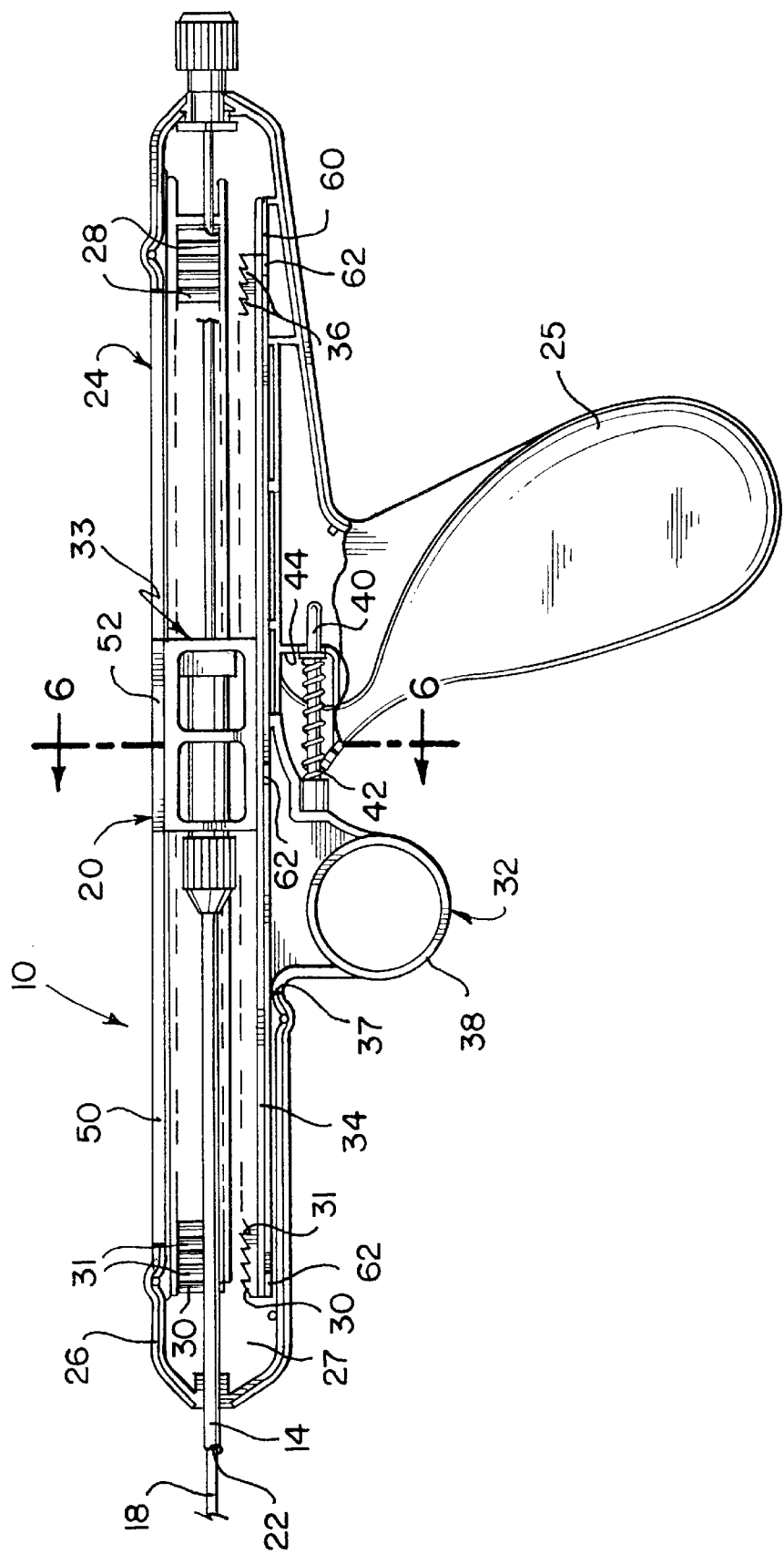
FIG. 3 is a sectional side view, in enlarged scale, of the mechanism shown in FIG. 1.

Referring now to FIGS. 1 through 3, there is shown a mechanism 10 for incrementally displacing one or more electrodes 12 according to one illustrative embodiment of the invention. In one illustrative embodiment, the electrode (s) 12 is carried on a movable member 14, for example, a catheter shaft or slidable sheath 16 which is slidably extended and retracted over an inner tubular member 18, for example, a guide wire, catheter shaft, or the like. An incremental displacement mechanism, generally designated 20, is connected to the movable member 14 and is operative, upon each actuation thereof, to displace the movable member, and thus the electrode, a predetermined distance relative to the inner member 18 and the mechanism 10. Thus, for example, in an ablation procedure, the device 10 may be manipulated through a patient's blood vessels by means of the guide wire or catheter shaft until the movable member 14 and electrode 12 are disposed in a desired location, such as in contact with an "active site" in the heart. Ablation energy is delivered to the electrode to destroy the adjacent tissue. The clinician then actuates the displacement mechanism 20 to incrementally move the movable member 14 and thus the electrode 12 a predetermined, known distance. The process is repeated one or more times to create a continuous lesion.

While two electrodes 12 are shown on the movable member 14, it will be apparent to those skilled in the art that the movable member may carry virtually any number of electrodes, for example, one or more. Preferably, one electrode will be disposed at the distal end of the member 14, with the other electrodes being disposed at spaced apart locations along the member.

Referring to FIG. 1, the movable member 14 is preferably in the form of a tubular shaft, which is flexible for manipulation through a patient's blood vessels and to a site of interest. The tubular shaft defines an interior lumen 22 which is sized to slidably receive the inner member 18 therethrough. The inner member may take many different forms, such as a guide wire having a preformed curve, and can be slidably inserted through the lumen 22 to impart a desired bend to a portion of the movable member, with the movable member and guide wire then being advanced together through the patient's blood vessels to a desired site, as is well known to those skilled in the art.

The medical device 10 further comprises a housing 24 which houses a portion of the inner member 18 and movable member 14 therein, and also houses the displacement mechanism 20 therein. The displacement mechanism is movable relative to the housing, as is described in greater detail below. The housing includes a handle portion 25 which may be gripped by a user's hand, and an elongated barrel portion 26 connected to the upper end of the handle and which is open at either longitudinal end thereof for extension of the movable and tubular members 14 and 18 therethrough.

The housing 24 includes an interior side wall 27 with a row of teeth 28 formed along the longitudinal length of the wall (shown in fragment in FIG. 3), which cooperate with the displacement mechanism to incrementally displace the displacement mechanism relative to the housing, as is described in greater detail below. The teeth 28 include angled leading edges 30 which face toward the front of the housing 24, and stepped trailing edges 31 which face toward the rear of the housing.

Referring to FIGS. 3 through 6, one illustrative embodiment of the displacement mechanism 20 will be described. The displacement mechanism generally comprises a trigger mechanism 32 and ratchet mechanism 33. The trigger mechanism comprises an elongated bar 34 which, on an upper side thereof, defines a plurality of upwardly projecting ratchet teeth 36. The teeth include forwardly facing, angled edges 30, and rearwardly facing, stepped edges 31, similar to the teeth 28 formed in the side wall 26 of the housing 24.

The bar 34 is connected on its lower side to a circular ring 38 defining a trigger, which extends downwardly through an opening 37 formed in the lower end of the housing 24. Extending rearwardly from the back side of the trigger 38 is a cylindrical rod 40, which is housed inside of the housing 24 for movement relative to the housing, and which slidably receives a compression spring 42 over it. The rearward end of the spring abuts against an internal stop 44 formed in the housing 24. Thus, when the trigger is squeezed (i.e., driven rearwardly relative to the housing), the spring is compressed. When the user then releases the trigger, the compression spring urges the trigger mechanism 32 back to its original position with the trigger 38 abutting against the forward end of the opening 37 (shown in FIG. 3).

The ratchet mechanism 33 is slidably housed in the housing 24 and engaged with the trigger mechanism 32 in such a manner that actuation of the trigger mechanism causes the ratchet mechanism to move rearwardly relative to the housing. However, when the trigger is released and driven forwardly relative to the housing 24 by the spring 42, the ratchet mechanism does not move forwardly, but rather remains in place relative to the housing. The structure achieving such function is now described in detail. The ratchet mechanism includes a resilient, flexible bottom tab 46 and a resilient, flexible side tab 48, which are designed to ride along, respectively, the row of teeth 36 formed on the trigger mechanism, and the row of side teeth 28 formed in the side wall 27 of the housing 24. The bottom tab and side tab angle outwardly from the ratchet body and toward the front of the housing 24. Thus, as described above, when the trigger 38 is squeezed, the trigger mechanism 32 is driven rearwardly relative to the housing 24. One of the stepped trailing edges 31 of the trigger mechanism teeth 36 engages the bottom tab 46 of the ratchet mechanism 33 and forces the ratchet mechanism 33 rearwardly. At the same time, the side tab 48 is driven rearwardly over one or more of the angled forward edges 30 of the side wall teeth 28. When the trigger is released, the spring urges the trigger mechanism toward the front of the housing 24. The bottom tab 46 then slides over the angled edges 30 of the trigger mechanism teeth 36 as they are driven forwardly relative to the housing, while the side tab 48 engages one of the stepped edges 31 of the side wall teeth 28 and is thereby prevented from moving forward relative to the housing 24. Thus, upon each actuation of the trigger 38, the ratchet mechanism 33 is displaced rearwardly a predetermined distance relative to the housing, but when the trigger is released, the side wall teeth act to keep the ratchet mechanism in place relative to the housing. The distance of the displacement is dependent on the travel path of the trigger 38. Preferably, the ratchet mechanism is displaced the length of one tooth 28 with each squeeze of the trigger 38. Therefore, in order to alter the length of the incremental displacement, the length of the teeth may be adjusted. Alternatively, the travel path of the trigger 38 can be altered so that the ratchet mechanism 33 is displaced a multiple number of teeth upon each squeeze of the trigger, such as two or more.

Referring now to FIG. 6, the internal structure of the housing 24 is shown in detail. The housing includes an elongated slot 50 formed in the upper wall of the housing, and slidably receives an upwardly and rearwardly projecting arm 52 of the ratchet mechanism 33.

With continued reference to FIG. 6, the upper interior walls of the housing 24 have a stepped configuration (as indicated by reference numerals 55 and 56) to complement the configuration of the upper surface portion of the ratchet mechanism 33, and define a track to allow the ratchet mechanism to slide through the housing, and guide the ratchet mechanism along a linear travel path inside the housing.

The housing 24 further includes a pair of elongated, internal recesses defining a pair of tracks 60 (FIG. 6), with one disposed on either lateral side of the housing. The trigger mechanism 32 includes a plurality of spaced apart, laterally outwardly projecting tabs or followers 62 which project outwardly from either side of the bar 34 and are formed having a complementary size to be slidably received in the respective tracks. Thus, the tracks and tabs cooperate to define a linear travel path for the trigger mechanism through the housing, and provide stability for the trigger mechanism as it is displaced relative to the housing 24.

As is well known to those skilled in the art, electrodes have different "damage ranges", which depend on the design and dimensions of the electrode. "Damage range" is defined herein to mean the area of tissue which is scarred when ablation energy is delivered to the electrode. Typically, the damage range is slightly larger than the surface area of the electrode contacting the tissue, and depends on electrode thickness, the electrode material, and the like. Thus, depending upon the type of electrode used, the length of the incremental displacement will vary. Because the damage range tends to approximate the length of the electrode, the length of the incremental displacement will preferably approximate the length of the electrode itself. It may even be preferably made slightly shorter than the length of the electrode to ensure overlapping damage ranges and therefore a continuous lesion. However, in the case of an electrode having a large damage range, the length of the incremental displacement can be longer than the length of the electrode.

In the embodiment shown in FIGS. 1 through 6, the ratchet mechanism 33 is connected to an outer sheath 14 which is slidable over an inner member 18. However, it will be apparent to those skilled in the art that the ratchet mechanism could alternatively be engaged directly to a catheter shaft with an electrode mounted on the catheter shaft.

It will also be apparent to those skilled in the art that the orientation of the teeth and springs could be reversed, to cause the ratchet mechanism 33 to be advanced toward the front of the housing 24 rather than be driven toward the rear of the housing. However, it is presently preferred to retract the ratchet mechanism and thus the movable member 14, for performing drag ablation procedures and the like.

In operation, the movable member 14 and inner member 18 are manipulated through the patient's vasculature to an intended site, such as an "active site". A power supply (not shown) is configured to energize the electrode 12 through an electrical conductor (not shown) in either a constant voltage, power, or temperature mode, as is well known in the art. Radio-frequency energy is delivered to the electrode 12 to ablate the tissue in close proximity to the electrode. Energy flows from the electrode 12 through the tissue to a return plate (not shown), which is connected to the ground potential of the power supply, to complete the circuit, as is well known to those skilled in the art. The flow of current through the tissue to the return plate causes heating which results in the destruction of the tissue near the electrode 12 (the electrode's damage range).

As described above, in the case of a relatively long active site, a long, continuous lesion must be formed. In order to create such a lesion, the clinician simply manipulates the medical device 10 until the ablation electrode 12 comes into contact with the patient's tissue and is located at one end of the active site. Ablation energy, for example, RF energy, is then delivered to the electrode 12, and the electrode is maintained in that location for an amount of time sufficient to ablate the adjacent tissue, as is known in the art. The clinician then squeezes and releases the trigger 38, so that the ratchet mechanism 33, and thus the movable member 14 and electrode 12, is displaced a predetermined distance. Once the electrode is in the new location, ablation energy is again delivered to the electrode 12 so that it ablates the adjacent tissue. This procedure is repeated one or more times to create the continuous lesion, without requiring the clinician to perform a drag procedure or to estimate the distance the electrode has been displaced.

Referring now to FIGS. 7 and 8, there is shown another illustrative embodiment of the mechanism 10 of the present invention. In that embodiment, the slidable electrode 100 is connected to an inner mandrel, shaft, or other tubular member 102. The member 102 is slidably received inside of an outer tubular sheath 104 which is formed having a longitudinal slot 106 formed in the side wall thereof. The electrode 100 is connected to the member 102 through a laterally extending connector 108 which is sized for passing through the slot 106. In all other respects, this embodiment is similar to the embodiment disclosed in FIGS. 1 through 6, with the ratchet mechanism 33 connected to the member 102 rather than to the outer member 104.

From the foregoing, it will be apparent to those skilled in the art that the present invention provides a medical device which facilitates the creation of continuous lesions, without requiring an elongated electrode that hinders the flexibility of the medical device, and without requiring that the clinician perform a drag procedure in which the clinician would have to estimate the distance the electrode was displaced. In addition, the medical device of the present invention provides an easily actuated mechanism for displacing an electrode to facilitate creating continuous lesions.

Having thus described preferred embodiments of the present invention, it is to be understood that the above described arrangement and system is merely illustrative of the principles of the present invention, and that other arrangements and systems may be devised by those skilled in the art without departing from the spirit and scope of the invention as claimed below.

What is claimed is:

1. A medical device having an incrementally displaceable electrode, comprising
    an elongated shaft,
    at least one electrode connected to the shaft,
    a housing receiving the proximal end of the shaft,
    a manually movable actuator in the housing, said actuator engaging the shaft such that movement of the actuator a first predetermined distance from an initial position relative to the housing causes the shaft and electrode to move linearly without rotation a second predetermined distance relative to the housing to a second position, and
    means for holding the shaft after it has moved the predetermined distance to said second position when the actuator is released and returned to its initial position, whereby the electrode can be moved by predetermined linear increments each time the actuator is moved the first predetermined distance.

2. A medical device according to claim 1, including a spring for biasing said actuator to said initial position, the engagement of the actuator and shaft being such that after the shaft has moved to said second position, the actuator can be moved relative to the shaft while the shaft is held in said second position.

3. A medical device according to claim 1, wherein the length of said second predetermined distance is based upon the damage range of the electrode.

4. A medical device according to claim 2, wherein the length of said second predetermined distance is based upon the damage range of the electrode.

5. A medical device according to claim 2, wherein said means for holding the shaft comprises a series of teeth-like projections and a projecting tab adapted to engage said teeth-like projections, one of said teeth-like projections and tab being connected to the housing and the other being connected to the shaft, whereby engagement of the tab and one of the teeth-like projections holds the shaft in its second position.

6. A medical device according to claim 5, wherein said teeth-like projections are connected to the housing and said tab is connected to said shaft.

7. A medical device according to claim 5, wherein said actuator is in the form of a trigger.

8. A medical device according to claim 2, wherein said shaft is connected to the actuator by a mechanism which permits movement of the shaft relative to the actuator in one direction only.

9. A medical device according to claim 5, wherein said shaft is connected to the actuator by a mechanism which permits movement of the shaft relative to the actuator in one direction only.

10. A medical device according to claim 8, wherein said mechanism comprises a series of teeth connected to the actuator and a second tab engaging the shaft, the teeth engaging said tab when the actuator is moved said first predetermined distance but being movable relative to the tab when the actuator is returned to its initial position.

11. A medical device according to claim 9, wherein said mechanism comprises a series of teeth connected to the actuator and a second tab engaging the shaft, the teeth engaging said tab when the actuator is moved said first predetermined distance but being movable relative to the tab when the actuator is returned to its initial position.

12. A medical device according to claim 2, further including an outer sheath connected to the housing, said shaft extending through said sheath, and the electrode being incrementally moveable on the outer surface of said sheath.

* * * * *